US010851477B2

(12) United States Patent
Bauerfeind

(10) Patent No.: US 10,851,477 B2
(45) Date of Patent: Dec. 1, 2020

(54) FIBERS AND YARNS WITH BLOCKING FUNCTION

(71) Applicant: Bauerfeind AG, Zeulenroda-Triebes (DE)

(72) Inventor: Hans B. Bauerfeind, Zeulenroda-Triebes (DE)

(73) Assignee: Bauerfeind AG, Zeulenroda-Triebes (DE)

( * ) Notice: Subject to any disclaimer, the term of this patent is extended or adjusted under 35 U.S.C. 154(b) by 785 days.

(21) Appl. No.: 15/127,302

(22) PCT Filed: Mar. 13, 2015

(86) PCT No.: PCT/EP2015/055318
§ 371 (c)(1),
(2) Date: May 26, 2017

(87) PCT Pub. No.: WO2015/140072
PCT Pub. Date: Sep. 24, 2015

(65) Prior Publication Data
US 2017/0306531 A1 Oct. 26, 2017

(30) Foreign Application Priority Data

Mar. 19, 2014 (DE) ........................ 10 2014 004 258

(51) Int. Cl.
| | | |
|---|---|---|
| *D01F 1/10* | (2006.01) | |
| *C08K 5/00* | (2006.01) | |
| *A61K 9/70* | (2006.01) | |
| *A61F 13/08* | (2006.01) | |
| *A61K 8/02* | (2006.01) | |
| *A61K 8/34* | (2006.01) | |
| *A61K 8/73* | (2006.01) | |
| *A61K 31/164* | (2006.01) | |
| *A61K 31/704* | (2006.01) | |
| *A61L 15/28* | (2006.01) | |
| *A61L 24/08* | (2006.01) | |
| *A61Q 19/00* | (2006.01) | |
| *D01F 2/02* | (2006.01) | |
| *A41B 9/00* | (2006.01) | |
| *A41B 9/06* | (2006.01) | |
| *A41B 11/00* | (2006.01) | |
| *A41B 17/00* | (2006.01) | |

(52) U.S. Cl.
CPC .............. *D01F 1/10* (2013.01); *A61F 13/08* (2013.01); *A61K 8/027* (2013.01); *A61K 8/345* (2013.01); *A61K 8/731* (2013.01); *A61K 9/70* (2013.01); *A61K 31/164* (2013.01); *A61K 31/704* (2013.01); *A61L 15/28* (2013.01); *A61L 24/08* (2013.01); *A61Q 19/007* (2013.01); *C08K 5/0008* (2013.01); *D01F 2/02* (2013.01); *A41B 9/001* (2013.01); *A41B 9/06* (2013.01); *A41B 11/00* (2013.01); *A41B 17/00* (2013.01); *A41B 2500/30* (2013.01); *A61L 2430/36* (2013.01); *D10B 2501/02* (2013.01); *D10B 2501/021* (2013.01); *D10B 2501/041* (2013.01); *D10B 2509/00* (2013.01); *D10B 2509/022* (2013.01)

(58) Field of Classification Search
None
See application file for complete search history.

(56) References Cited

U.S. PATENT DOCUMENTS

| | | | | |
|---|---|---|---|---|
| 5,217,780 A | * | 6/1993 | Wurzer ................ | A47G 9/0238 139/420 R |
| 5,232,769 A | * | 8/1993 | Yamato ................ | A41B 17/00 2/239 |
| 7,422,712 B2 | | 9/2008 | Delucia et al. | |
| 2001/0007671 A1 | | 7/2001 | Gueret | |
| 2003/0186611 A1 | | 10/2003 | Zikeli et al. | |
| 2005/0287106 A1 | | 12/2005 | Legendre | |
| 2006/0019571 A1 | * | 1/2006 | Lange ...................... | D04H 1/42 442/402 |
| 2010/0162541 A1 | * | 7/2010 | Luo ....................... | D04H 1/4258 28/105 |
| 2011/0045078 A1 | * | 2/2011 | Kolbe ...................... | A61K 9/70 424/488 |

FOREIGN PATENT DOCUMENTS

| | | |
|---|---|---|
| CN | 102995295 A | 3/2013 |
| CN | 103225172 A | 7/2013 |
| DE | 69909029 T2 | 3/2000 |
| DE | 100 07 794.3 A1 | 6/2001 |
| DE | 602005001306 T2 | 3/2006 |

(Continued)

OTHER PUBLICATIONS

English Translation of International Preliminary Report on Patentability and Written Opinion of the International Searching Authority, dated Sep. 20, 2016 from related PCT International Application No. PCT/EP2015/055318.
Decision to Grant—Related Application 2016140728/05 in Russia, dated Jul. 10, 2018.
Westphal, Thea, et al., "Medical compression stockings on the skin moisture in patients with chronic venous disease," Vasa (2019) 1-7, retrieved from http://doi.org/10.1024/0301-1526/a000812.
bauerfeind.com, "Evidence of improving skin properties through use of medical compression stockings with integrated skin care substances," 3 pages.
International Search Report from related application No. PCT/2015/055318, dated May 18, 2015.

(Continued)

*Primary Examiner* — Brian Gulledge
(74) *Attorney, Agent, or Firm* — Durham Jones & Pinegar; Sarah W. Matthews

(57) ABSTRACT

A polymer composition comprising a polymer and at least one active substance selected from the group consisting of a substance generating an occlusion, in particular a substance generating an internal occlusion or a substance generating an external occlusion; a moisturizing substance; a substance reducing pain or itching; and mixtures of these.

21 Claims, No Drawings

(56) References Cited

FOREIGN PATENT DOCUMENTS

| DE | 202004021745 U1 | 10/2010 |
|---|---|---|
| EP | 1345914 A1 | 9/2003 |
| GB | 1275969 | 6/1972 |
| GB | 2389853 A | 12/2003 |
| GB | 2414394 A | 11/2005 |
| JP | H08325831 A | 12/1996 |
| JP | H092960 A | 1/1997 |
| WO | 2009133059 A2 | 11/2009 |

OTHER PUBLICATIONS

Written Opinion of the International Searching Authority from related application No. PCT/2015/055318.
List of Prior art cited by the German patent office in related German application No. 10 2014 004 258.8.

* cited by examiner

FIBERS AND YARNS WITH BLOCKING FUNCTION

BACKGROUND

The present invention concerns a polymer composition comprising a polymer and at least one active substance; formed bodies having such a polymer composition; the use of the formed bodies and polymer compositions; and corresponding threads, non-woven materials, articles of clothing, and medical resources.

Polymer compositions that are "functionalized" by additives are known. For example, U.S. Pat. No. 5,766,746 thus describes cellulose fibers that include a flame-retardant component. DE 100 37 983 A1 describes polymer compositions having an alkaloid content, and DE 100 07 794 A1 describes polymer compositions having a material made from marine plants or marine animals.

Such polymer compositions are additionally processed to make threads, textile surfaces and articles of clothing.

The addition of additives for the functionalization of polymer fibers often times makes it problematic to maintain the properties necessary for use of the fibers—in particular mechanical strength, loop strength, fiber elongation, abrasion property and dye affinity.

However, there is a continuous demand for functional fibers and articles of clothing made from such fibers with specific additives, such that it is important to provide such fibers in which the described difficulties are overcome so that functionalized fibers may satisfy the corresponding requirements for the clothing article produced from them.

Additives that are particularly relevant to the market are in this respect additives having an effect on the organism of the wearer of the clothing articles produced from the polymer compositions.

Previously known structures include only low concentrations of these substances. These substances are applied via impregnation of or coating on the substrate matrix. For example, this leads to low washing resistances such that those substances must be regularly resupplied to maintain their mode of action.

SUMMARY OF INVENTION

Therefore, the present invention is based on the technical problem of providing a polymer composition that includes a corresponding additive, wherein a good stability and processibility of the formed body that is produced from the polymer composition nevertheless results.

For clothing articles and medical resources that rest close to the skin, for example bandages and compression stockings, a regulation of skin moisture plays a role in the wear comfort—in particular, a drying out of the skin should be prevented. Such textile surfaces should also not lead to skin drying and skin irritation, or exacerbate skin diseases, such as atopic dermatitis, that already exist. An itching or pain that is linked with such skin diseases should thereby also at least be reduced.

The technical problem forming the basis of the present invention is also the provision of clothing articles and medical resources, and their starting material, that are in particular improved in this regard.

The present invention solves its underlying technical problem via the subject matter of the independent claims.

In particular, the present invention solves its underlying technical problem via a polymer composition comprising a polymer and at least one active substance selected from the group consisting of a substance generating an occlusion, in particular a substance generating an internal occlusion or a substance generating an external occlusion; a substance contributing moisture; a substance reducing pain or itching; and mixtures of these.

According to one aspect of the invention, in addition to the polymer, the polymer composition thus additionally includes at least one active substance, wherein the active substance is a substance generating an occlusion, in particular a substance generating an internal occlusion or a substance generating an external occlusion; a substance contributing moisture; or a substance reducing pain or itching. Naturally, the presence of two or more of these substances and mixtures of these substances is encompassed by the invention.

It has surprisingly been shown that such active substances may be introduced into a polymer composition and may deploy their effect there as an additive, in particular directly on the adjoining skin, if the polymer composition rests on the skin in the form of corresponding products such as clothing articles and medical resources. In particular, these active substances may thereby prevent a drying of the skin and/or at least reduced pain and itching given illnesses such as atopic dermatitis. The active substances may also be used to allow additional active substances to penetrate into the skin.

Surprisingly, it could thereby also be established that the group of active substances according to the invention that are included as additives in the polymer composition has a good durability over its usage time period, and thus may deploy its effect over this time period.

Moreover, it has surprisingly been shown that the polymer compositions according to the invention lead to fibers—in particular if they include cellulose or are cellulose-based—that, in spite of the addition of at least one of the additives according to the invention, show the same excellent properties as pure fibers (in particular cellulose fibers), for example with regard to their fineness, tear strength, tear strength variation, elongation, wet expansion, tear strength as related to fineness, wet tear strength as related to fineness, loop tear strength as related to fineness, wet abrasion variation, and wet modulus. Nevertheless, these fibers simultaneously showed the positive properties imparted by at least one additive.

In some embodiments, the fibers are produced from a spinning solution. It has been shown that—in spite of the addition of at least one additive according to the invention—surprisingly no degradation of a spinning solution is produced, in particular if it includes cellulose, and especially if the spinning solution is made from cellulose, N-methylmorpholine-N-oxide (NMMNO) and water.

DETAILED DESCRIPTION

Suitable production methods for the claimed polymer compositions are known from DE 10 2007 054 702 A1, in particular for polymer compositions that include cellulose or modified cellulose, and in particular in the form of formed bodies.

The polymer composition may include polymers as they are typically used for the production of fibers, filaments, threads, non-woven materials, clothing articles, and medical resources such as bandages and compression stockings.

In one embodiment, the polymer is selected from the group consisting of cellulose, modified cellulose, polyamide, polyacrylic, polyester, polyurethane, polyethylene, polypropylene, modifications of these and mixtures of these.

In a preferred embodiment, the polymer is selected from the group consisting of cellulose, modified cellulose, polyamide, polyacrylic, polyester, modifications of these and mixtures of these.

In one embodiment, the polymer is biodegradable. The biodegradable polymer is in some embodiments selected from the group consisting of cellulose, modified cellulose, latex, albumen of vegetable or animal origin, and mixtures of these. Polycondensation and polymerization polymers, polyurethanes, polyesters, polyacrylics, and mixtures of these materials may also be used.

However, in an alternative embodiment, it may also be provided that the polymer composition according to the invention also includes polymers that are not biodegradable. Examples of such polymers are polyamides, aromatic polyamides (in particular aramides), polyacrylonitrile, polyester, or polyvinyl alcohols.

In a preferred embodiment, the polymer is cellulose, modified cellulose, or modifications of these and mixtures of these. In a preferred embodiment, the polymer is cellulose or modified cellulose.

Cellulose is a polymer, made up of a hydrophilic network, whose supramolecular structures are stabilized both in solution and in a solid via likewise hydrophilic hydrogen bonds. In contrast to this, the active substances that are used in the present invention are selected from the group consisting of substances generating an internal occlusion, substances generating an external occlusion, and moisturizing substances, which are at least nonpolar, lipophilic organic compounds. Within the scope of the present invention, it has now surprisingly been shown that such nonpolar, lipophilic active substances can be introduced into the cellulose filaments and fibers. It is likewise surprising that the nonpolar, lipophilic organic active substances that are incorporated into the hydrophilic cellulose network can be distributed homogeneously and in microparticle form, such that a precisely adjustable and uniform storage as well as controlled release of these nonpolar, lipophilic organic substances from the fibers is made possible.

The polymer composition according to the invention is in some embodiments produced from a spinning solution. The active substances are in some embodiments present as micro-inclusions in the polymer composition.

What is understood by modified cellulose is in particular carboxyethyl cellulose, methyl cellulose, nitrate cellulose, copper cellulose, viscose, i.e. cellulose xantoghenate, cellulose carbamate and cellulose acetate.

In an alternative embodiment, the polymer is a polyamide, a polyacrylic, a polyester, or modifications of these and mixtures of these. In another embodiment, the polymer is a polyamide or modifications thereof. In another embodiment, the polymer is a polyacrylic or modifications thereof. In another embodiment, the polymer is a polyester or modifications thereof.

Examples of polycondensation and polymerization polymers are polyamides that are substituted with methyl, hydroxy or benzyl groups, for example. Examples of polyurethanes are those that are synthesized on the basis of polyether polyols.

According to the invention, the polymer composition thus includes at least one active substance, wherein the active substance may be a substance generating an occlusion, in particular a substance generating an internal occlusion or a substance generating an external occlusion; a substance contributing moisture; or a substance reducing pain or itching; or mixtures of these.

The at least one active substance is in some embodiments incorporated into the polymer composition, and in particular is not applied onto the substrate matrix via impregnation or coating.

The polymer composition in some embodiments includes at least one active substance generating an occlusion, in particular a substance generating an internal occlusion or a substance generating an external occlusion.

In connection with the present invention, what is understood by occlusion is the prevention or reduction of water loss through the skin to the environment, for example to a textile padding.

In addition to further important functions, the human skin protects against assaults from the environment. To maintain its protective function, it is essentially important to avoid the loss of water from the lower layers of skin.

The structure of human skin is divided in three components, namely the epidermis, the dermis and the subcutis. With their keratin filaments, the outer layers of the stratum corneum of the epidermis play a particular role in the water content of the skin. The keratin fibrous scaffold thus can hold considerable quantities of water. The target and point of application of the external occlusive effect of a corresponding substance is the epidermis. The major effect—namely the suppression of an escape of water (trans-epidermal water loss) from the stratum corneum—deploys via application of such a substance onto the skin surface. A film that prevents the escape of moisture is formed via these substances. Given the outer occlusion, water may thus move up from the lower layers and fill the keratin fibrous scaffold of the outer epidermis with moisture. The stratum corneum thereby protects against drying out. Elasticity and flexibility of the skin are maintained, and the skin achieves its physiological equilibrium for protection, for example against fungal infection. This occlusive mode of action of an active substance is also designated as external occlusion.

Internal occlusion designates a change to the skin lipid configuration in the stratum corneum. In the hexagonal configuration, the hydrocarbon chains of the lipid may rotate freely about their axis. This phase of "loose packing" achieves a more porous, thus permeable, structure and facilitates an unwanted release of water in the stratum corneum under stress, with corresponding disadvantageous consequences, such as dry skin. Given the inner occlusion, a denser ortho-rhombic packing of the lipids is generated via the action of specific active substances. This arrangement leads to a more rigid structure. Due to the "ortho-rhombic packing" of the lipids, such a molecular action produces significantly less permeability of the skin barrier, and thus significantly reduces the water loss from the stratum corneum.

In one embodiment, the at least one active substance generates an internal occlusion.

The at least one active substance generating an internal occlusion is in some embodiments a fatty acid derivative. The fatty acid derivative is in some embodiments selected from the group consisting of isostearyl isostearate, isopropyl palmitate, and mixtures of these. The fatty acid derivative is in some embodiments isostearyl isostearate. Alternatively, the fatty acid derivative is in some embodiments isopropyl palmitate.

In an alternative embodiment, the at least one active substance generates an external occlusion.

The at least one active substance generating an external occlusion is in some embodiments selected from the group consisting of higher molecular alkanoic acids, higher molecular alkenoic acids, higher molecular carbonates, and mixtures of these. The at least one active substance generating an external occlusion is in some embodiments selected from the group consisting of cetearyl isononanoate, dicaprylyl carbonate, and mixtures of these. The active substance is in some embodiments cetearyl isononanoate. The active substance is in some embodiments dicaprylyl carbonate.

In an alternative embodiment, the at least one active substance is a substance contributing moisture.

The at least one moisturizing active substance is in some embodiments selected from the group consisting of glycerin, polyols, in particular panthenol, and other moisturizing substances such as urea. The at least one moisturizing active substance is in some embodiments glycerol (propane-1,2,3-triol).

The at least one active substance reducing pain or itching is in some embodiments a fatty acid amide compound, a modification thereof or a derivative thereof, or a flavonoid, a modification thereof or a derivative thereof.

The at least one active substance reducing pain or itching is in some embodiments selected from the group consisting of palmitoylethanolamine (PEA), stearoylethanolamide (SEA), oxerutin, troxerutin, and mixtures of these.

The at least one active substance reducing pain or itching is in some embodiments an N-acylethanolamine (NAE).

The at least one active substance reducing pain or itching is in some embodiments a palmitoylethanolamine (PEA) or stearoylethanolamide (SEA).

The naturally occurring fatty amides PEA and its homologs, such as the closely related SEA, exhibit very good anti-inflammatory properties. They are thus used as lipid components in cosmetic formulations such as, for example, anti-dry scalp shampoo products. However, these substances are also used against influenza viruses, common cold illnesses, respiratory illnesses and rheumatic fever. The substances are also administered as an oral administration with pain-relieving property. These substances generally demonstrate an itch-reducing, pain-relieving and anti-inflammatory effect. The human epidermis may be irritated by both harmful environmental influences and continuous irritations; for example, it may be attacked by textile surfaces. The subjective sensation of itching and pain arises as a result of this. The active physiological mechanism may be explained as follows: pain and inflammation stimuli (triggered by a textile surface, for example) strike receptors for pain relaying, and the activation of the inflammation receptors of the mast cells leads to the discharge of strongly inflammatory histamines. The result is, first, the triggering of pain sensation due to relaying from the sensory nerve fibers of the skin to the relevant areas of the brain. Second, the release of the inflammatory substances in the epidermis leads to an itching, reddening and dryness of the skin. The assault by PEA and its homologs achieves palliation at the molecular level, due to two mechanisms: on the one hand, PEA and its homologs are mast cell modulators. The histamine release by the mast cells is blocked by increased PEA concentrations at the site of the inflammation. On the other hand, PEA and its homologs have a high affinity to the receptors responsible for pain and inflammation. This leads to a suppression of the corresponding irritation signaling. If acting on affected skin areas, PEA and its homologs thus show an anti-inflammatory, calming effect on dry, itchy and irritated skin.

The at least one active substance reducing pain or itching is in some embodiments a flavonoid, a modification thereof or a derivative thereof. The at least one active substance reducing pain or itching is in some embodiments a rutin, a modification thereof or a derivative thereof.

The at least one active substance reducing pain or itching is in some embodiments rutin, oxerutin or troxerutin, a modification thereof or a derivative thereof. The at least one active substance reducing pain or itching is in some embodiments troxerutin, a modification thereof or a derivative thereof. The at least one active substance reducing pain or itching is in some embodiments troxerutin.

Troxerutin is a vegetable substance from the flavonoid group and is used for treating illnesses that are accompanied by an increased permeability of the blood vessels. Venous illnesses that are accompanied by water retention in tissue, i.e. edemas, are to be cited here. Belonging among these are, for example, surface venous inflammations or varicose veins, as well as venous weakness during pregnancy. Rutins, for example troxerutin, are also applied to open leg wounds, chronic venous insufficiency and given heavy, tired legs or leg cramps that are to be attributed to a blockage of the leg veins. In addition to a damage to the inner vessel walls, blood clots, blockages and inflammation arise given congestion in the veins. Inner vessel wall damage is caused by substances that release white blood cells during inflammation. Troxerutin prevents the release of these substances and thus stabilizes the permeable vessel walls of the blood capillaries. These are sealed such that fluid can no longer exit them. Moreover, troxerutin improves the flow properties of the blood in that it makes the red blood cells more elastic and has a slightly anti-coagulative effect. Given congestions in the veins, the sum of these effects contributes to less water escaping into the surrounding tissue and forming edemas. Symptoms of these venous illnesses, such as pain and a feeling of heaviness in the legs, are alleviated in this way via the application of troxerutin.

In an alternative embodiment, the polymer composition includes at least one active substance generating an occlusion, in particular a substance generating an internal occlusion or a substance generating an external occlusion, and at least one active substance reducing pain or itching.

In an alternative embodiment, the polymer composition includes at least one moisturizing active substance and at least one active substance reducing pain or itching.

In an alternative embodiment, the polymer composition includes at least one active substance generating an occlusion, in particular a substance generating an internal occlusion or a substance generating an external occlusion, and at least one moisturizing active substance.

In an alternative embodiment, the polymer composition includes at least one active substance generating an occlusion, in particular a substance generating an internal occlusion or a substance generating an external occlusion; at least one active substance reducing pain or itching; and at least one moisturizing active substance.

The present invention also concerns a formed body or a plurality of formed bodies comprising a polymer composition according to the invention.

One advantage of the formed body according to the invention in which the additives according to the invention are comprised is the uniform incorporation of the active substances into the formed body, in particular into the fiber matrix, given different fiber cross sections that can be produced. Processing as a monofilament thread or continuous filament thread is in this respect also possible, facilitating its use for technical articles.

The formed body according to the invention may be used for the most varied purposes.

The formed body is in some embodiments a fiber. The fiber is in some embodiments a staple fiber, a monofilament, a multifilament or a continuous multifilament.

In particular if the fiber is a cellulose fiber, for example, it can be constructed as shown in FIGS. 1 and 2 of DE 10 2007 054 702 A1. The at least one active substance may be present in the form of dispersed inclusions in a matrix, in particular a cellulose matrix.

The at least one active substance is in some embodiments stabilized with at least one hydrophobic thickening agent.

In particular, if a textile surface is produced from the fibers according to the invention, this may not only be comprised of the fibers according to the invention but may also include additional components, for example wool, lyocell, rayon, carbacell, polyester, polyamide, cellulose acetate, acrylate, polypropylene, or mixtures of these.

The present invention also concerns the use of a formed body according to the invention for the production of threads.

The present invention also concerns a thread including a formed body according to the invention. The present invention also concerns a thread including the formed bodies according to the invention as a basic component. The present invention also concerns a thread comprised of formed bodies according to the invention.

The present invention also concerns a non-woven material including a formed body according to the invention. The present invention also concerns a non-woven material including a thread according to the invention.

The present invention also concerns a clothing article or a medical resource including a formed body according to the invention or a thread according to the invention. These are in some embodiments clothing articles or medical resources that, at least in part, rest directly on the skin when worn.

The present invention also concerns a clothing article including a formed body according to the invention or a thread according to the invention. The clothing article is in some embodiments underclothes, in particular underpants, an undershirt or a stocking. Alternatively, the clothing article may also be a glove.

The present invention also concerns a medical resource including a formed body according to the invention or a thread according to the invention. The medical resource is in some embodiments a compression stocking or a bandage.

The present invention also concerns a sport bandage and other sport resources including a formed body according to the invention or a thread according to the invention.

The present invention also concerns the use of a polymer composition according to the invention or a formed body according to the invention in a clothing article, in a sport resource or in a medical resource for skin care.

The present invention also concerns the use of a polymer composition according to the invention or a formed body according to the invention in a clothing article, in a sport resource or in a medical resource to prevent skin from drying out.

The present invention also concerns the use of a polymer composition according to the invention or a formed body according to the invention in a clothing article, in a sport resource or in a medical resource, to reduce pain and/or itching, in particular given damaged skin and skin diseases such as atopic dermatitis. At the same time, a drying out of the skin is thereby preferably reduced or prevented.

The invention claimed is:

1. A clothing thing article or medical resource comprising a thread comprising a cellulose polymer and at least one active substance selected cetearyl isononanoate; dicaprylyl carbonate; isostearyl isostearate; isopropyl palmitate; a moisturizing substance selected from glycerol polyols, panthenol, urea, and mixtures of these; a substance reducing pain or itching selected from palmitoylethanolamine (PEA), stearoylethanol amide (SEA), oxerutin, troxerutin, and mixtures of these; and mixtures of these, wherein the active substance is distributed homogeneously in microparticle form within the cellulose polymer.

2. The clothing article or medical resource comprising a thread according to claim 1, wherein the at least one active substance is a nonpolar substance.

3. The clothing article or medical resource comprising a thread according to claim 1, wherein the moisturizing substance is glycerol.

4. The clothing article or medical resource comprising a thread according to claim 1, wherein the thread comprises a fiber, the fiber being selected from the group consisting of a staple fiber, a monofilament, a multifilament, a continuous multifilament, and combinations thereof.

5. The clothing article or medical resource of claim 1, wherein the active substance is not applied to the cellulose polymer via impregnation.

6. The clothing article or medical resource of claim 1, the thread comprising the cellulose polymer and at least one active substance, the at least one active substance resistant to washing away from the cellulose polymer.

7. The clothing article or medical resource of claim 1, wherein the clothing article or medical resource comprises the clothing article.

8. The clothing article or medical resource of claim 7, wherein the clothing article comprises at least one of an underpant, an undershirt, a stocking, and a glove.

9. The clothing article or medical resource of claim 1, wherein the clothing article or medical resource comprises the medical resource.

10. The clothing article or medical resource of claim 9, wherein the medical resource comprises at least one of bandages and compression stockings.

11. The clothing article of claim 7, wherein the cetearyl isononanoate is not applied onto the cellulose polymer via impregnation or coating.

12. A clothing article or medical resource comprising a thread, the thread comprising a cellulose; at least one of cetearyl isononanoate, dicaprylyl carbonate, isostearyl isostearate, and isopropyl palmitate; wherein the at least one of cetearyl isononanoate, dicaprylyl carbonate, isostearyl isostearate, and isopropyl palmitate is distributed homogeneously in microparticle form within the cellulose polymer.

13. The clothing article or medical resource comprising a thread of claim 12, further comprising at least one selected from the group of moisturizing substance, a substance reducing pain or itching, and mixtures of these.

14. The clothing article or medical resource comprising a thread of claim 12, wherein the thread is woven into a fiber.

15. The clothing article or medical resource comprising a thread according to claim 14, wherein the fiber is selected from the group consisting of a staple fiber, a monofilament, a multifilament or a continuous multifilament.

16. A clothing article or medical resource comprising a thread comprising a cellulose polymer; at least one of cetearyl isononanoate, dicaprylyl carbonate, isostearyl isostearate, and isopropyl palmitate; at least one moisturizing substance; and at least one substance reducing pain or itching, wherein the at least one of cetearyl isononanoate, dicaprylyl carbonate, isostearyl isostearate, and isopropyl palmitate is distributed homogeneously in microparticle form within the cellulose polymer.

17. A clothing article or medical resource comprising a thread according to claim 16, wherein the at least one moisturizing substance is selected from the group consisting of glycerol, polyols, in particular panthenol, and urea.

18. A clothing article or medical resource comprising a thread according to claim 17, wherein the at least one moisturizing active substance is glycerol.

19. A clothing article or medical resource comprising a thread according to claim 16, wherein the substance for reducing pain or itching is a fatty acid amide compound, or a modification thereof or a derivative thereof, a flavonoid, or a modification thereof or a derivative thereof.

20. A clothing article or medical resource comprising a thread according to claim 16, wherein the substance for reducing pain or itching is selected from the group consisting of palmitoylethanolamine (PEA), stearoylethanolamide (SEA), oxerutin, troxerutin, and mixtures of these.

21. A clothing article comprising a plurality of threads, the plurality of threads comprising a cellulose polymer functionalized with cetearyl isononanoate, the cetearyl isononanoate distributed homogeneously in microparticle form within the cellulose polymer.

* * * * *